United States Patent [19]
Amadio et al.

[11] Patent Number: 6,043,399
[45] Date of Patent: Mar. 28, 2000

[54] PROCESS FOR THE PREPARATION OF CUMENE HYDROPEROXIDE

[75] Inventors: Joao Amadio; Brice Le Corre; Jean-Jacques Charrin, all of Lyons; Xavier Houzard, Bron; Philippe Laurent, Roussillon; Roland Noyerie, Salaise-sur-Sanne; Yves-Michel Quenton, Saintes-Colombes, all of France

[73] Assignee: Rhodia Chimie, Courbevoie, France

[21] Appl. No.: 09/252,596

[22] Filed: Feb. 12, 1999

Related U.S. Application Data

[63] Continuation of application No. 08/591,550, filed as application No. PCT/FR94/00990, Aug. 8, 1994, abandoned.

[51] Int. Cl.[7] .................................................. C07C 407/00
[52] U.S. Cl. ........................... 568/574; 568/385; 568/798
[58] Field of Search ..................................... 568/574, 385, 568/798

[56] References Cited

U.S. PATENT DOCUMENTS 4,262,143   4/1981   Becker ...................................... 568/574

FOREIGN PATENT DOCUMENTS 0032758   7/1981   European Pat. Off. ............... 568/574
3287574   12/1991   Japan ...................................... 568/574

*Primary Examiner*—James H. Reamer
*Attorney, Agent, or Firm*—Jean-Louis Seugnet

[57] ABSTRACT

The present invention lies in the field of the manufacture of phenol from cumene. The subject of the invention is a process for the continuous preparation of cumene hydroperoxide by oxidation, in the liquid phase, of cumene in the presence of oxygen. The process according to the invention is carried out in the presence of at least one agent chosen from the hydroxide or the carbonate of an alkali metal and/or alkaline-earth metal; the said agent being used in an amount of between 2 and 10 ppb (expressed as sodium hydroxide) with respect to the amount of cumene introduced. The invention likewise relates to the use of the hydroperoxide thus obtained for preparing phenol.

9 Claims, No Drawings

PROCESS FOR THE PREPARATION OF CUMENE HYDROPEROXIDE

This application is a continuation application of U.S. application Ser. No. 08/591,550, filed on Jan. 06, 1998 now abandoned, which is a Continued Prosecution Application of Ser. No. 08/591,550, filed on Apr. 10, 1996 now abandoned, which is an application under 35 U.S.C. Section 371 of International Application Number PCT/FR94/00990, filed Aug. 08, 1994.

The present invention lies in the field of the manufacture of phenol from cumene. More particularly, the present invention relates to the first stage of this process, namely the production of cumene hydroperoxide.

The production of phenol from cumene is a well known industrial process carried out continuously and comprising essentially two stages.

The first consists in oxidizing cumene to cumene hydroperoxide in the liquid phase, using a gas containing oxygen. The hydroperoxide thus obtained is then, in a second stage, decomposed to give phenol and acetone.

Before this second stage, it is necessary to concentrate the hydroperoxide formed. In fact, for reasons of efficiency of the process and of safety, the oxidation reaction of the cumene is not carried out beyond a certain concentration of hydroperoxide in the reaction mixture. The reason is to avoid premature cleavage of the hydroperoxide formed, which can become uncontrollable. The hydroperoxide content of the reaction mixture generally does not exceed 40% by weight, hence the necessity of a concentration stage prior to cleavage to phenol.

During the first part of the process, cumene hydroperoxide is formed at the same time as various by-products such as, in particular dimethylphenylcarbinol, dicumyl peroxide or acetophenone, as well as phenol and organic acids. The presence of the latter compounds is recognized as harmful to the reaction. In fact, the acids promote cleavage of the hydroperoxide to phenol, which is itself an inhibitor of the oxidation reaction.

For this reason, many processes recommend carrying out the oxidation reaction of cumene in the presence of various additives, such as in particular agents which neutralize the said compounds, agents chosen in general from the hydroxide or the carbonate of an alkali metal or alternatively an alkali metal salt of cumene hydroperoxide.

A first type of process for the preparation of cumene hydroperoxide consists in carrying out the reaction in the presence of a neutralizing agent in amounts of the order of a few percent. These processes, however, have disadvantages due to the use of relatively significant contents of such agents.

On the one hand, these amounts represent a not insignificant additional raw material cost for the process.

On the other hand, they require the use of additional equipment before the stage of concentration of the cumene hydroperoxide. In fact, it is recalled that the use of additives of this type produces alkali metal salts which must be removed from the reaction mixture before the concentration stage in order to avoid fouling the equipment used during this concentration stage. Now, this operation is only possible by washing the reaction mixture one or a number of times with water. However, such a method requires the use of a preconcentration stage of the washed reaction mixture, before the actual stage of concentration of the hydroperoxide.

Another means could be envisaged for removing the alkali metal salts, such as filtration of the reaction mixture. However, the amounts of agent used in the known processes make it impossible to use such a method on an industrial scale, because the filters are very quickly fouled by deposition or the salts and therefore become unusable. Moreover, this separation operation is relatively problematic because the filtered salts have a viscous consistency which makes the filtration itself and then the subsequent cleaning of the filters difficult to carry out.

Finally, safety problems may occur because the said salts are unstable and can spontaneously ignite on exposure to air.

A second type of process for the preparation of cumene hydroperoxide consists in carrying out the reaction with a neutralizing agent employed in amounts of the order of a few hundreds of tarts per million with respect to the cumene present in the medium. Such a process is in particular described in Japanese Patent Application JP 3,287,574. However, this process is implemented at a high pressure.

Another known type of process for the preparation of cumene hydroperoxide consists in carrying out the oxidation of cumene without addition of a neutralizing agent. However, when, in the course of the reaction, the acidity increases in the reactor(s) where the said reaction is taking place, it is recommended that certain operating characteristics of the process be modified in order to return to favourable reaction conditions. Thus, it is possible to lower the temperature, all the other reaction parameters being kept constant, but with the disadvantage of reducing the oxidation rate and consequently the productivity of the process. Another possible route would be to increase the temperature in order to retain good productivity. However, in such a case, this would be achieved to the detriment of the selectivity and probably of safety, as a result of possible premature cleavage of the cumene hydroperoxide manufactured.

The problem of controlling the hydroperoxide preparation reaction temperature has been treated in particular in European Patent Application EP 32758. Thus, when the temperature is observed to be drifting, it is recommended to add 0.05 to 20 g of a basic substance per tonne of the reaction mixture. Additionally, it is shown that the temperature of the reaction must preferably be lowered. However, this reference only deals in concrete terms with the case of the production of ethylbenzene hydroperoxide, a less reactive compound than cumene.

The aim of the present invention is therefore to overcome the disadvantages mentioned of the known processes for the preparation of phenol from cumene and more particularly of the oxidation stage of cumene. Thus, the process according to the invention makes it possible to implement the above-mentioned oxidation reaction with significant oxidation rates, without it being necessary, in order to maintain these oxidation rates, for the reaction to be placed, even transitorily, under conditions which are less favourable to productivity. Moreover, the process according to the invention makes it possible to be freed from problems of fouling of the filters placed before the stage of concentration of the hydroperoxide formed.

These aims and others are achieved by the present invention which therefore relates to a process for the continuous preparation of cumene hydroperoxide by oxidation, in the liquid phase, of a reaction mixture comprising cumene, in the presence of a gas containing oxygen, characterized in that the oxidation reaction is carried cut in the presence of at least one agent chosen from the hydroxide or the carbonate of an alkali metal and/or alkaline-earth metal; the said agent being used in an amount of between 2 and 10 ppb (expressed as sodium hydroxide) with respect to the amount of cumene introduced.

It was entirely surprisingly found that amounts as low as those indicated above were sufficient to maintain industrially exploitable oxidation conditions. By way of comparison, the concentrations of neutralizing agent in the reaction mixture were considerably nigher according to the prior art, usually between 0.1 and a few %.

Moreover, as a result of the presence of the said agent, it is no Longer necessary, in order to maintain stable operating conditions, to vary the reaction parameters out simply to adjust the amount of neutralizing agent.

Other advantages and characteristics will, however, become more clearly apparent on reading the description and examples which will follow.

As was indicated previously, the process for the preparation of phenol from cumene comprises two main stages, oxidation of cumene to hydroperoxide and then decomposition of the said peroxide to a mixture of acetone and phenol.

The oxidation reaction of cumene is generally carried out in one or a number of devices in series (or oxidizers). More particularly, the oxidation reaction is carried out in two to eight devices.

The reaction mixture at the outlet of the last oxidizer is treated so as to remove the traces of alkali metal salts which are found therein. Any method known to those skilled in the art could be used. However, in a particularly advantageous way, separation of the salts from the reaction mixture is carried out by using the filtration method.

The reaction mixture is then treated in order, on the one hand, to separate the unreacted cumene from the cumene hydroperoxide and, on the other hand, to concentrate the said peroxide until a content of this compound, in the outflow, of approximately 80 to 85% is obtained.

This operation can be carried out in one or a number of stages. Use is conventionally made of the principle of distillation under vacuum, in one or a number of fractionation columns.

The concentrated hydroperoxide flow is then decomposed to phenol and to acetone.

During the first stage of the process, cumene is oxidized by a gas containing oxygen, in one or a number of stages.

The cumene introduced into the oxidizers consists partly of fresh cumene and partly of recycled cumene.

In fact, as indicated above, not all the cumene introduced is converted to hydroperoxide. Generally, the degree of conversion of the cumene is between 20 and 40%. Also, for obvious reasons of economy, recycling of the unreacted cumene in the process is generally provided for.

The proportion of recycled cumene is not critical and those skilled in the art are able to adjust the latter.

Whatever the nature of the cumene (fresh cumene or recycled cumene), the latter preferably has a purity of at least 99.5% and more particularly of at least 99.8%.

Moreover, the cumene is substantially free of acid and of phenol.

Thus, the unreacted cumene is treated before being introduced into the process, in order to free it of any impurity which it contains, and more particularly of acid impurities.

The cumene is conventionally subjected to one or a number of washing cycles, each stage being followed by a separation by settling. In a first step, treatment is carried cut with an aqueous solution of a base chosen in particular from alkali metal or alkaline-earth metal hydroxides. The concentration of these solutions is between 10 and 20%. The cumene thus treated is then subjected to one or a number of washing with water/separation by settling stages, in order to remove all remaining traces of alkali metal or alkaline-earth metal salts.

These operations are generally undertaken at a temperature lying between 25 and 45° C.

It should be noted that the process according to the invention does not promote the formation of by-products, such as in particular phenol. Consequently, the content of pollutants, which are mainly found in the wash liquors of the cumene, is reduced, consequently facilitating their purification.

The oxidation reaction is carried out in the presence of a gas containing oxygen. For this purpose, it is possible to use any pure or dilute oxygen source, such as air, optionally enriched in oxygen. Air is advantageously used as the oxidizing agent of cumene.

Each of the oxidizers is equipped with means for introducing gas containing oxygen. Generally, and in order to optimize the quality of the liquid/gas mixing, introduction of oxygen is carried out at the foot of the oxidizers, by any means known to those skilled in the art.

The oxygen content introduced into the reaction mixture is at least 8% and preferably at least 20%.

Generally, and for reasons of safety, the amount of oxygen in the gases departing from each of the oxidizers is kept below 6.5%. More particularly, the amount of oxygen is kept between 2 and 6.5% and preferably between 4.5 and 6.5%.

The essential characteristic of the invention lies in the fact that an agent chosen from the hydroxide or the carbonate of an alkali metal and/or alkaline-earth metal is introduced into the oxidizers; the said agent being used in an amount which is considerably lower that that of the known processes since it is between 2 and 10 ppb (expressed as sodium hydroxide) with respect to the amount of cumene introduced.

The amount of agent introduced is preferably between 2 and 5 ppb (expressed as sodium hydroxide).

The agent chosen is more particularly a compound based on an alkali metal, such as in particular sodium hydroxide, potassium hydroxide, sodium carbonate or Potassium carbonate.

The agent is brought into contact with the reaction mixture, Preferably in the form of an aqueous solution. The concentration of agent in the solution is such that it allows the concentration range of 2 to 10 ppb (expressed as sodium hydroxide) in the said mixture to be respected.

Introduction of the agent can be carried out continuously or non-continuously, in one or each of the oxidizers. In the latter case, the total amount of agent in the reaction mixture does not exceed 10 ppb (expressed as sodium hydroxide) with respect to the amount of cumene introduced.

The agent is injected so that the pH of the reaction mixture remains between 3 and 5.

The resonance time of the reaction mixture in each of the oxidizers is between 10 and 48 hours.

The reaction temperature is between 70 and 110° C. Preferably, the temperature is between 75 and 90° C.

It should be noted that the reaction temperature conventionally varies within the oxidizers and more particularly that it decreases when the concentration of cumene hydroperoxide increases.

This measurement, known to those skilled in the art, is necessary to avoid any risk of premature decomposition of the peroxide and to retain a good yield.

The oxidation reaction can be carried out at atmospheric pressure or under a slight positive pressure. Thus, the oxidation can suitably be carried out at a pressure between 1 and 3 bar absolute.

The reaction mixture after the successive oxidation stage (s) s filtered in order to remove the traces of alkali metal and/or alkaline-earth metal salts. Surprisingly, fouling of the filters due to the fact that the oxidation reaction of the cumene was carried out in the presence of an alkali metal or alkaline-earth metal agent was not observed. Thus, the process according to the invention makes it possible to use filters on an industrial scale and thus introduces a significant simplification of the stage of separation of the alkali metal or alkaline-earth metal salts from the reaction mixture.

The reaction mixture thus treated is then fractionated and concentrated by distillation under vacuum, carried out in one or a number of stages.

The cumene recovered at the conclusion of this distillation's recycled to the oxidizers, after having been purified according to the method indicated previously.

Cumene hydroperoxide is obtained with a concentration of approximately 85%.

Cleavage of the hydroperoxide to phenol and to acetone is then carried out according to conditions well known to those skilled in the art.

Concrete but non-limiting examples of the process according to the invention will now be presented.

EXAMPLE

The oxidation stage is carried out in a continuous steel reactor, with a total volume equal to 8 liters, continuously supplied with a washed cumene solution containing 0.1% CHPO (cumene hydroperoxide), air and an aqueous sodium hydroxide solution.

The impact of a shutdown in the sodium hydroxide supply is revealed by the fall in the CHPO assay and the increase in the phenol assay and acidity: the temperature must be increased in order to retain productivity. This modification leads to an additional deterioration of the reaction mass.

The amounts of sodium hydroxide injected in order to re-establish a normal oxidation profile are very low: of the order of 5 ppb of 100% sodium hydroxide. This enables the unit to operate with remarkable reliability without damaging the performances of the concentration and distillation devices downstream.

These results are presented in the following table:

What is claimed is:

1. A process for the continuous preparation of cumene hydroperoxide by oxidation, in a liquid phase, of a reaction mixture comprising cumene in the presence of a gas containing oxygen, wherein the oxidation reaction is carried out at a temperature of between 75 and 90° C. at a pressure of between 1 and 3 bar absolute in the presence of at least one agent selected from the group consisting of a hydroxide or a carbonate of an alkali metal or alkaline-earth metal; said agent being used in an amount of between about 2 and about 10 ppb (expressed as sodium hydroxide) with respect to the amount of cumene introduced.

2. A process according to claim 1, wherein said amount of agent is between about 2 ppb (expressed as sodium hydroxide) with respect to the amount of cumene introduced.

3. A process according to claim 1, wherein said agent is chosen from the group consisting of sodium hydroxide, potassium hydroxide, sodium carbonate or potassium carbonate.

4. A process according to claim 1, wherein use is made of a cumene flow with a purity of at least about 99.5%.

5. A process according to claim 1, wherein use is made of a cumene flow which is substantially free of acid and of phenol.

6. A process according to claim 1, wherein use is made of a reaction mixture comprising at least about 8% of oxygen.

7. The process of claim 4, wherein cumene has a purity of at least about 99.8%.

8. The process of claim 1, wherein said reaction mixture comprises at least about 20% oxygen.

9. The process of preparation of phenol comprising the steps of:
   a) preparing continuously cumene hydroperoxide by oxidation, in a liquid phase, of a reaction mixture comprising cumene, in the presence of a gas containing oxygen, wherein the oxidation reaction is carried out at a temperature of between 75 and 90° C. at a pressure of between 1 and 3 bar absolute in the presence of at least one agent selected from the group consisting of a hydroxide of an alkali metal, a carbonate of an alkali metal, a hydroxide of an alkali-earth metal, a carbonate of an alkali-earth metal and mixtures thereof;
   b) decomposing the cumene hydroperoxide obtained in step (a) in phenol and acetone; and
   c) isolating phenol from the mixture of phenol and acetone.

| Time interval (h) | Cumene (kg/h) | Sodium hydroxide (mg/h) | T (° C.) | CHPO (%) | pH | Phenol (ppm) | Acidity (ppm) | $O_2$ (%) |
|---|---|---|---|---|---|---|---|---|
| 0–62 | 0.1 | $5.10^{-4}$ | 78.2 | 30.1 | 3.6 | 4 | 30 | 6.2 |
| 62–124 | 0.1 | 0 | 80 | 29.5 | — | 4 | 30 | 6.2 |
| 124–186 | 0.1 | 0 | 80.6 | 27.3 | 3.3 | 28 | 55 | 6.5 |
| 186–248 | 0.1 | $5.10^{-4}$ | 78.3 | 27.9 | 3.9 | 8 | 30 | 3.0 |
| 248–310 | 0.1 | $5.10^{-4}$ | 78 | 29 | 3.8 | 4 | 25 | 5.8 |